(12) United States Patent
Cully et al.

(10) Patent No.: US 9,901,715 B2
(45) Date of Patent: Feb. 27, 2018

(54) RETRACTABLE SHEATH DEVICES, SYSTEMS, AND METHODS

(71) Applicant: W. L. Gore & Associates, Inc., Newark, DE (US)

(72) Inventors: Edward H. Cully, Flagstaff, AZ (US); Peter Heicksen, Flagstaff, AZ (US)

(73) Assignee: W. L. Gore Associates, Inc., Newark, DE (US)

( * ) Notice: Subject to any disclaimer, the term of this patent is extended or adjusted under 35 U.S.C. 154(b) by 0 days.

(21) Appl. No.: 14/018,202

(22) Filed: Sep. 4, 2013

(65) Prior Publication Data

US 2014/0066898 A1    Mar. 6, 2014

Related U.S. Application Data

(60) Provisional application No. 61/697,269, filed on Sep. 5, 2012, provisional application No. 61/789,949, filed on Mar. 15, 2013.

(51) Int. Cl.
*A61M 25/00* (2006.01)
*A61M 25/10* (2013.01)
(Continued)

(52) U.S. Cl.
CPC ........... *A61M 25/10* (2013.01); *A61L 29/041* (2013.01); *A61L 29/085* (2013.01); *A61L 29/146* (2013.01);
(Continued)

(58) Field of Classification Search
CPC .................. A61M 25/10; A61M 31/00; A61M 2025/1081; A61M 2025/0057;
(Continued)

(56) References Cited

U.S. PATENT DOCUMENTS

| 4,193,138 A | 3/1980 | Okita |
| 4,902,423 A | 2/1990 | Bacino |

(Continued)

FOREIGN PATENT DOCUMENTS

| CN | 101437467 A | 5/2009 |
| CN | 101795630 | 8/2010 |

(Continued)

OTHER PUBLICATIONS

Salzmann, et al. Effects of balloon dilatation on ePTFE structural characteristics. J Biomed Mater Res Sep. 15, 1997; 36(4) :498-507.
(Continued)

*Primary Examiner* — Scott Medway
(74) *Attorney, Agent, or Firm* — Kilpatrick Townsend & Stockton, LLP

(57) ABSTRACT

The invention is directed to delivery medical devices that enable consistent "on-demand" delivery of therapeutic agents to a vessel. The medical device of the current invention comprises retractable sheath comprising neckable elements. The design and methods disclosed herein ensures that therapeutic agent delivery occurs essentially only upon necking of the outer sheath, minimizing coating and/or therapeutic agent loss to the bloodstream and providing controlled delivery to the treatment site.

20 Claims, 11 Drawing Sheets

(51) Int. Cl.
*A61L 29/08* (2006.01)
*A61L 29/14* (2006.01)
*A61L 29/16* (2006.01)
*A61L 29/04* (2006.01)
*A61F 2/962* (2013.01)
*A61F 2/958* (2013.01)

(52) U.S. Cl.
CPC ............... *A61L 29/16* (2013.01); *A61F 2/962* (2013.01); *A61F 2002/9583* (2013.01); *A61M 2025/105* (2013.01); *A61M 2025/1081* (2013.01); *A61M 2025/1086* (2013.01)

(58) Field of Classification Search
CPC .. A61M 2025/1075; A61M 2025/1086; A61M 25/1038
USPC ......................................... 604/103.01, 103.02
See application file for complete search history.

(56) References Cited

U.S. PATENT DOCUMENTS

| | | | |
|---|---|---|---|
| 4,994,072 A * | 2/1991 | Bhate | A61M 25/1006 604/917 |
| 5,049,275 A | 9/1991 | Gillberg-LaForce et al. | |
| 5,066,298 A | 11/1991 | Hess | |
| 5,074,871 A | 12/1991 | Groshong | |
| 5,091,205 A | 2/1992 | Fan | |
| 5,211,654 A * | 5/1993 | Kaltenbach | 606/191 |
| 5,213,576 A * | 5/1993 | Abiuso et al. | 604/103.01 |
| 5,232,444 A * | 8/1993 | Just et al. | 604/110 |
| 5,269,755 A | 12/1993 | Bodicky | |
| 5,304,121 A * | 4/1994 | Sahatjian | A61F 2/90 604/103.02 |
| 5,318,531 A | 6/1994 | Leone | |
| 5,458,568 A | 10/1995 | Racchini et al. | |
| 5,476,589 A | 12/1995 | Bacino | |
| 5,478,349 A | 12/1995 | Nicholas | |
| 5,571,086 A * | 11/1996 | Kaplan | A61B 8/12 604/96.01 |
| 5,599,306 A * | 2/1997 | Klein | A61M 25/104 604/103.01 |
| 5,609,629 A | 3/1997 | Fearnot et al. | |
| 5,616,119 A | 4/1997 | Davis | |
| 5,693,014 A * | 12/1997 | Abele | A61M 25/1002 604/103.08 |
| 5,773,019 A | 6/1998 | Ashton et al. | |
| 5,868,704 A | 2/1999 | Campbell et al. | |
| 5,893,840 A | 4/1999 | Hull et al. | |
| 5,902,745 A | 5/1999 | Butler et al. | |
| 5,954,706 A | 9/1999 | Sahatjian | |
| 5,964,730 A * | 10/1999 | Williams | A61M 25/10 604/103 |
| 6,001,386 A | 12/1999 | Ashton et al. | |
| 6,096,070 A | 8/2000 | Ragheb et al. | |
| 6,120,477 A * | 9/2000 | Campbell | A61F 2/958 604/96.01 |
| 6,149,641 A * | 11/2000 | Ungs | A61K 31/565 604/103.01 |
| 6,280,411 B1 | 8/2001 | Lennox | |
| 6,306,166 B1 | 10/2001 | Barry et al. | |
| 6,364,856 B1 | 4/2002 | Ding et al. | |
| 6,395,208 B1 | 5/2002 | Herweck et al. | |
| 6,447,540 B1 | 9/2002 | Fontaine | |
| 6,450,989 B2 * | 9/2002 | Dubrul et al. | 604/104 |
| 6,524,274 B1 | 2/2003 | Rosenthal et al. | |
| 6,544,222 B1 | 4/2003 | Yang | |
| 6,716,444 B1 | 4/2004 | Castro | |
| 6,733,474 B2 | 5/2004 | Kusleika | |
| 6,753,071 B1 | 6/2004 | Pacetti | |
| 6,939,320 B2 | 9/2005 | Lennox | |
| 6,939,374 B2 | 9/2005 | Banik et al. | |
| 6,955,661 B1 | 10/2005 | Herweck et al. | |
| 7,020,529 B2 | 3/2006 | Krall et al. | |
| 7,066,904 B2 | 6/2006 | Rosenthal et al. | |
| 7,179,251 B2 | 2/2007 | Palasis | |
| 7,572,245 B2 | 8/2009 | Herweck et al. | |
| 7,637,886 B2 | 12/2009 | Herweck et al. | |
| 7,713,573 B2 * | 5/2010 | Owens | A61F 2/07 427/2.1 |
| 7,740,793 B2 | 6/2010 | Herweck et al. | |
| 7,811,622 B2 | 10/2010 | Bates et al. | |
| 7,871,659 B2 | 1/2011 | Cook | |
| 7,875,284 B2 | 1/2011 | Reyes et al. | |
| 7,892,201 B1 * | 2/2011 | Laguna et al. | 604/96.01 |
| 7,919,108 B2 | 4/2011 | Reyes et al. | |
| 7,947,015 B2 | 5/2011 | Herweck et al. | |
| 8,048,440 B2 | 11/2011 | Chang et al. | |
| 8,048,503 B2 | 11/2011 | Farnsworth et al. | |
| 8,062,270 B2 | 11/2011 | Sweeney | |
| 8,114,049 B2 | 2/2012 | Freyman et al. | |
| 8,162,880 B2 | 4/2012 | Jayaraman | |
| 8,177,743 B2 | 5/2012 | Lennox | |
| 8,398,703 B2 | 3/2013 | Kassab et al. | |
| 2002/0077693 A1 | 6/2002 | Barclay et al. | |
| 2003/0028210 A1 * | 2/2003 | Boyle | A61F 2/82 606/192 |
| 2004/0230316 A1 | 11/2004 | Cioanta et al. | |
| 2004/0247640 A1 * | 12/2004 | Zhao | A61K 47/48992 424/423 |
| 2005/0085841 A1 | 4/2005 | Eversull et al. | |
| 2005/0182361 A1 | 8/2005 | Lennox | |
| 2006/0190022 A1 * | 8/2006 | Beyar | A61F 2/958 606/192 |
| 2006/0253072 A1 | 11/2006 | Pai et al. | |
| 2008/0015500 A1 | 1/2008 | Herweck et al. | |
| 2008/0021385 A1 | 1/2008 | Barry et al. | |
| 2008/0033476 A1 | 2/2008 | Greene | |
| 2008/0118544 A1 | 5/2008 | Wang | |
| 2008/0140002 A1 | 6/2008 | Ramzipoor et al. | |
| 2008/0213463 A1 | 9/2008 | Cook et al. | |
| 2009/0076448 A1 | 3/2009 | Consigny et al. | |
| 2009/0226502 A1 | 9/2009 | Chen | |
| 2009/0227948 A1 | 9/2009 | Chen et al. | |
| 2009/0227949 A1 * | 9/2009 | Knapp | A61L 29/085 604/103.02 |
| 2009/0264975 A1 | 10/2009 | Flanagan et al. | |
| 2009/0287182 A1 | 11/2009 | Bishop et al. | |
| 2010/0021519 A1 | 1/2010 | Shenoy | |
| 2010/0042199 A1 | 2/2010 | Burton | |
| 2010/0049225 A1 | 2/2010 | To et al. | |
| 2010/0209472 A1 | 8/2010 | Wang | |
| 2010/0228333 A1 | 9/2010 | Drasler et al. | |
| 2011/0015725 A1 | 1/2011 | Bates et al. | |
| 2011/0054396 A1 * | 3/2011 | Kangas | A61L 29/14 604/103.02 |
| 2011/0137244 A1 | 6/2011 | Lee et al. | |
| 2011/0190863 A1 | 8/2011 | Ostroot et al. | |
| 2011/0196340 A1 | 8/2011 | Barry et al. | |
| 2011/0251582 A1 | 10/2011 | Lennox | |
| 2011/0270226 A1 | 11/2011 | Kocur et al. | |
| 2011/0301565 A1 | 12/2011 | Weber | |
| 2012/0035283 A9 | 2/2012 | Xu et al. | |
| 2012/0053517 A1 | 3/2012 | Chen et al. | |
| 2012/0283820 A1 | 11/2012 | Tseng et al. | |
| 2013/0103062 A1 | 4/2013 | To et al. | |
| 2013/0158675 A1 | 6/2013 | Hutchins, III et al. | |
| 2013/0226131 A1 * | 8/2013 | Bacino | A61L 29/146 604/500 |
| 2013/0253426 A1 * | 9/2013 | Campbell | A61M 25/10 604/103.02 |

FOREIGN PATENT DOCUMENTS

| | | |
|---|---|---|
| EP | 0565604 | 7/1999 |
| EP | 0708671 | 11/2001 |
| EP | 0747069 | 9/2002 |
| EP | 0863729 | 12/2004 |
| EP | 0920843 | 2/2005 |
| EP | 1263492 | 4/2005 |
| EP | 0836429 | 11/2005 |
| EP | 1148899 | 4/2006 |

(56) References Cited

FOREIGN PATENT DOCUMENTS

| | | |
|---|---|---|
| EP | 1351739 | 5/2006 |
| EP | 1800702 | 6/2007 |
| EP | 1011743 | 7/2011 |
| EP | 2043704 | 8/2011 |
| WO | 96/40305 | 12/1996 |
| WO | 01/64278 | 9/2001 |
| WO | 03/015677 | 2/2003 |
| WO | 2008/064058 | 5/2008 |
| WO | WO-2009/111716 A1 | 9/2009 |
| WO | 2010/093800 | 8/2010 |
| WO | 2013/074185 | 5/2013 |

OTHER PUBLICATIONS

International Search Report for PCT/US2013/058171 dated Dec. 16, 2013, corresponding to U.S. Appl. No. 14/018,053, 4 pages.
International Search Report for PCT/US2013/058242 dated Dec. 19, 2013, corresponding to U.S. Appl. No. 14/018,202, 4 pages.

* cited by examiner

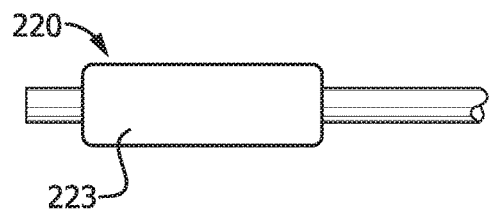
FIG. 2E
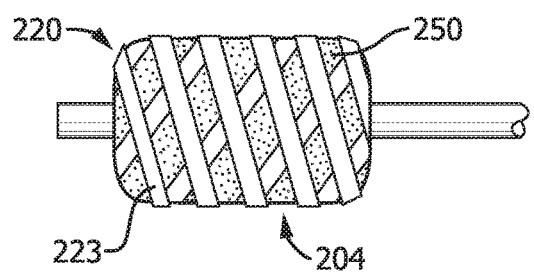
FIG. 2F
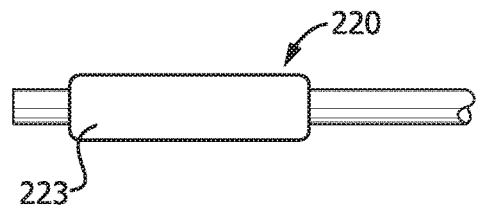
FIG. 2G
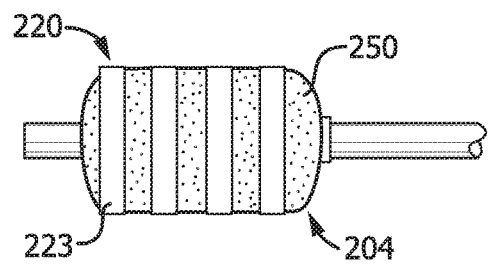
FIG. 2H
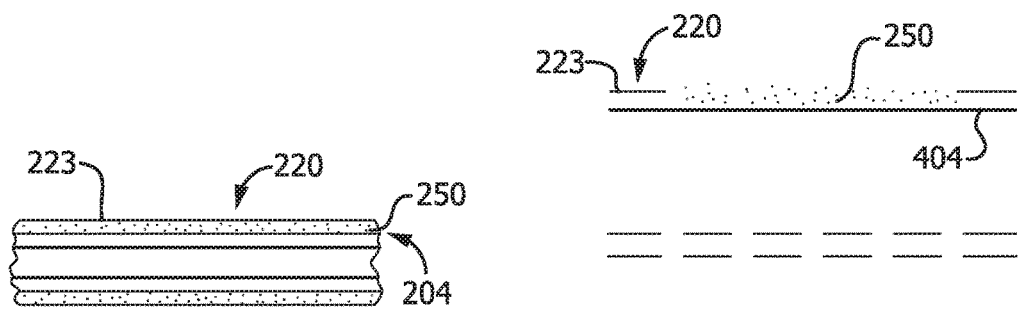
FIG. 2I
FIG. 2J

RETRACTABLE SHEATH DEVICES, SYSTEMS, AND METHODS

BACKGROUND

The systemic administration of therapeutic agents treats the body as a whole even though the disease to be treated may be localized. In some cases of localized disease, systemic administration may not be desirable because the drug agents may have unwanted effects on parts of the body which are not to be treated or because treatment of the diseased part of the body requires a high concentration of a drug agent that may not be achievable by systemic administration.

It is therefore often desirable to administer therapeutic agents to only localized sites within the body. Common examples of where this is needed include cases of localized disease (e.g., coronary heart disease) and occlusions, lesions, or other disease in body lumens. Several devices and methods for localized drug delivery are known. In one example, such devices are drug delivery balloons, and methods of their use include the steps of coating a balloon attached to a balloon catheter with a drug and a carrier matrix, inserting the catheter into a blood vessel, tracking the balloon to a desired location, and expanding the balloon against the surrounding tissue to transfer the drug locally at the intended treatment site.

One of the potential drawbacks to localized drug delivery is the possibility of premature or unintended release of the drug, the carrier matrix, and/or the drug/carrier matrix combination. This may occur during tracking and placement at the treatment site of a drug delivery device and post delivery as the device is withdrawn from the body. Such unintended release may result from drug diffusion, device contact with areas proximate the treatment site, or washing of the drug from the surface of the delivery device due to blood flow. This is of particular concern when the device comprises a therapeutic agent of a type or dosage not intended to be released to tissue or blood outside the treatment site.

Drugs or coating components shed in this unwanted fashion may be in particulate form or may be in solution. The downstream release of undesirable particles is known as "particulation". For example, particulation of large particles can create problems such as ischemia in tissues, especially in tissues supplied by small diameter vessels. Furthermore, the resulting effects of biodistribution of such particles are not well understood and may result in adverse effects.

In view of the potential drawbacks to current, localized drug delivery, there exists a need for devices and methods that allow for controlled, localized delivery of drug agents to specific treatment sites within a mammalian body that avoids premature or unintended drug release away from the intended treatment site.

SUMMARY

The present disclosure is directed to an expandable medical device that has a neckable, outer sheath that enables localized, on-demand delivery of a therapeutic agent to a vessel or other lumen of cavity, while not substantially delivering or releasing said therapeutic agent as the device is being tracked to or positioned at the desired treatment site. The medical device of the current invention comprises an expandable member with at least one coating comprising at least one therapeutic agent on the expandable member. The outer sheath comprises at least one neckable element forming said sheath that, through necking of the material upon expansion of the expandable member, the underlying coating is exposed to the surrounding environment. Neckable elements prevent undesired release of a therapeutic agent and/or prevent particulation during tracking. Prior to inflation, the sheath prevents release of said therapeutic agent.

In an embodiment, the invention comprises a medical device comprising an expandable member and a retracting sheath disposed around said expandable member. Said sheath can comprise one or more "neckable" elements. Said elements cover the expandable member at a first state, for example, in an un- or partially-inflated state. As the sheath is expanded or further expanded, said elements become strained and assume a second state, decreasing in width and increasing in overall length. The transition from first toward second state serves to open or move the sheath and uncover the underlying expandable member. In various embodiments, at least about 60% of the surface of the underlying expandable member is uncovered or exposed. In various embodiments, at least about 75% of the surface of the underlying expandable member is uncovered or exposed. In various embodiments, at least about 85% of the surface of the underlying expandable member is uncovered or exposed. In various embodiments, at least about 90% of the surface of the underlying expandable member is uncovered or exposed. Said sheath can comprise at least one helically wrapped, neckable element; at least two adjacent annular, neckable elements; or at least two longitudinal, neckable elements. In an embodiment, the sheath is comprised of a netting or weave of neckable filaments where the interstitial spaces open upon stretching. In an embodiment, the width of said sheath element decreases upon expansion of an expandable member. In another embodiment, the length of said sheath element increases upon expansion of an expandable member. In an embodiment, said medical device further comprises a coating having a therapeutic agent. In an embodiment, said coating can be located between the sheath and the expandable member. In another embodiment, said coating comprises a hydrophilic agent. In another embodiment, said coating comprises at least one compound selected from the group consisting of benzethonium chloride, poloxamer-188, polyethylene glycol, calcium salicylate, and hydroxypropyl-β-cyclodextrin. In another embodiment, said therapeutic agent is a hydrophobic agent. In another embodiment, said therapeutic agent comprises paclitaxel. In a further embodiment, said coating and therapeutic agent are disposed between the surface of the expandable member and the sheath and when said expandable member expands, said sheath allows rapid transfer of said coating and therapeutic agent through the sheath to an area external to said sheath. In one embodiment, said expandable member is a medical balloon. In another embodiment, said medical device comprises a catheter. In another embodiment, said sheath comprises an expanded fluoropolymer. In another embodiment, said neckable elements comprises a microstructure comprised interconnected fibrils or interconnected nodes and fibrils. In another embodiment, said sheath comprises expanded polytetrafluoroethylene (ePTFE). In another embodiment, said expandable member further comprises a structural layer. In another embodiment, said structural layer comprises said therapeutic agent. In constructing the above embodiment, a coating can be applied to the outer surface of the neckable elements that make up the sheath. Once applied, the sheath can be everted so that the outer surface becomes the inner surface and is disposed about the expandable member.

In another embodiment, a medical device can comprise a retracting sheath that covers an underlying surface and can comprise neckable elements, wherein when said expandable member and sheath are expanded, said neckable elements neck and said underlying surface is exposed. Said elements cover the expandable member at a first state, for example, in an un- or partially-inflated state. As the sheath is expanded or further expanded, said elements become strained and assume a second state, decreasing in width and increasing in overall length. The transition from first toward second state serves to open or move the sheath and uncover the underlying surface. Said sheath can comprise at least one helically wrapped, neckable element; at least two adjacent annular, neckable elements; or at least two longitudinal, neckable elements. In an embodiment, the width of said sheath element decreases upon expansion of an expandable member. In another embodiment, the length of said sheath element increases upon expansion of an expandable member. In an embodiment, said medical device further comprises a coating having a therapeutic agent. In an embodiment, said coating can be on the underlying surface. In one embodiment, upon expansion, said therapeutic agent is transferred to tissue.

Another embodiment of the invention comprises a balloon catheter comprising a balloon comprising a coating and a therapeutic agent disposed around the outer surface of said balloon, and a retracting sheath disposed around said balloon. Said sheath can comprise at least one neckable element. Said elements cover the expandable member at a first state, for example, in an un- or partially-inflated state. As the sheath is expanded or further expanded, said elements become strained and assume a second state, decreasing in width and increasing in overall length. The transition from first toward second state serves to open or move the sheath and uncover the underlying balloon. In an embodiment, said balloon comprises a coating. Said sheath can comprise at least one helically wrapped, neckable element, at least two adjacent annular, neckable elements, or at least two longitudinal, neckable elements. In an embodiment, the width of said sheath element decreases upon expansion of the balloon. In another embodiment, the length of said sheath element increases upon expansion of balloon. In an embodiment, a coating comprising a therapeutic agent can be located between the sheath and the balloon. In another embodiment, said coating comprises a hydrophilic component. In another embodiment, said coating comprises a hydrophilic agent. In an embodiment, the therapeutic agent is the hydrophilic agent. In another embodiment, said coating comprises at least one compound selected from the group consisting of benzethonium chloride, poloxamer-188, polyethylene glycol, calcium salicylate, and hydroxypropyl-β-cyclodextrin. In another embodiment, said therapeutic agent is a hydrophobic agent. In another embodiment, said therapeutic agent comprises paclitaxel. In another embodiment, said medical device comprises a catheter. In another embodiment, said sheath comprises a fluoropolymer. In another embodiment, said sheath comprises a microstructure comprised of interconnected fibrils and/or nodes interconnected by fibrils. In another embodiment, said sheath comprises an expanded polymer, such as expanded polytetrafluoroethylene (ePTFE). In another embodiment, said expandable member further comprises a structural layer. In another embodiment, said structural layer comprises said coating and therapeutic agent. In constructing the above embodiment, a coating can be applied to the outer surface of the neckable elements that make up the sheath. Once applied, the sheath can be everted so that the outer surface becomes the inner surface and is disposed about the balloon.

Another embodiment of the invention comprises a balloon catheter comprising: a balloon comprising a coating disposed on or within the outer surface of said balloon; and an outer sheath disposed around said coating, said sheath forms openings, which expose sections of the underlying coating, and allows rapid transfer of said coating to a surrounding area. In an embodiment, said sheath comprises neckable elements. In an embodiment, said first sheath is configured to split or tear to form openings. In another embodiment, said first sheath can be folded or otherwise configured onto the balloon in such a way that a plurality of openings are not exposed through the thickness of said first sheath until expanded. In one embodiment, said coating is transferred through said second sheath and onto or into a target tissue. In an embodiment, said therapeutic agent remains substantially adhered to the target tissue for greater than 1 minute after contact between balloon and treatment site is substantially eliminated. In another embodiment, said first sheath has a microstructure composed of interconnected fibrils and/or nodes interconnected by fibrils. In an embodiment, said first sheath comprises a fluoropolymer. In an embodiment, said first sheath comprises ePTFE. In another embodiment, said therapeutic agent is a hydrophilic agent. In another embodiment, said therapeutic agent is a hydrophobic agent. In another embodiment, said therapeutic agent is paclitaxel. In another embodiment, said balloon further comprises a structural layer.

In another embodiment, the invention comprises a medical device comprising: an expandable member; an outer sheath disposed around said expandable member comprising a splittable, tubular casing, and a coating contained inside said splittable casing comprising a therapeutic agent. Upon expansion of the underlying expandable member, the splittable casing opens to expose the lumen to the surrounding tissue. In an embodiment, said casing has a microstructure composed of nodes interconnected by fibrils. In another embodiment, said casing comprises a fluoropolymer. In another embodiment, said casing comprises an expanded polymer such as ePTFE. In another embodiment, said nodes are aligned substantially parallel to the length (or longer dimensional) axis of said splittable casing and said fibrils are aligned at an angle which is not substantially parallel to said axis. In another embodiment, said nodes are aligned at an angle which is not substantially parallel to the length (or longer dimensional) axis of said casing and said fibrils are aligned substantially parallel to said axis. In another embodiment, said coating comprises a hydrophilic component. In another embodiment, said coating comprises a hydrophilic agent. In an embodiment, the therapeutic agent is the hydrophilic agent. In another embodiment, said coating comprises at least one compound selected from the group consisting of benzethonium chloride, poloxamer-188, polyethylene glycol, sodium salicylate, and hydroxypropyl-β-cyclodextrin. In another embodiment, said therapeutic agent is a hydrophobic agent. In another embodiment, said therapeutic agent is paclitaxel. In another embodiment, said therapeutic agent remains substantially adhered to the target tissue for greater than 1 minute after contact between expandable member and treatment site is substantially eliminated. In other embodiment, said casing can comprise an annular ring disposed about the expandable member. In an embodiment, a casing can be longitudinally oriented. In another embodiment, a plurality of said casings can be disposed about the expandable member. In another embodiment, said casing comprises a tearable seam along its length.

In another embodiment, said casing comprises a tearable seam around, or angled around its circumference. Said seam comprises a structurally weakened area, e.g., perforations, a thinning in the wall thickness, or the like. In another embodiment, the casing becomes strained as said expandable member expands facilitating splitting of the casing. In one embodiment, said expandable member is a medical balloon. In another embodiment, said medical device comprises a catheter. In another embodiment, the splittable casing can comprise film that prevents or limits unintended transfer of therapeutic agent through said casing.

In another embodiment, the invention comprises a medical device comprising: an expandable member; an outer sheath disposed around said expandable member comprising a tubular, neckable casing, and a therapeutic agent contained inside said casing as well as a second therapeutic agent located on a surface underlying the outer sheath. Said neckable casing has walls that initially prevent transfer of said therapeutic agent through said casing walls when said casing; wherein said therapeutic agent is disposed inside the casing; and wherein when said expandable member and neckable casing (serving as the sheath) are expanded, said casing tears or splits open allows the transfer of said therapeutic agent to an area external to said sheath. In addition, upon expansion, said neckable casing necks to at least partially expose the underlying second coating, which also allows the transfer of second therapeutic agent to an area external said sheath. In an embodiment, said casing has a microstructure composed of interconnected fibrils and/or nodes interconnected by fibrils. In various embodiments, said casing comprises a fluoropolymer. In another embodiment, said casing comprises an expanded polymer such as ePTFE. In various embodiments, the casing becomes strained as said expandable member expands facilitating splitting or tearing of the casing. In various embodiments, said casing can be helically wrapped around the expandable member. In other embodiment, said casing can comprise an annular ring disposed about the expandable member. In other embodiments, a casing can be longitudinally oriented. In various embodiments, a plurality of said casings can be disposed around the expandable member. In various embodiments, upon expansion of the expandable member said casing necks and exposes said second coating that is transferred onto or into a target tissue. In various embodiments, said both therapeutic agents remain substantially adhered to the target tissue for greater than 1 minute after contact between expandable member and treatment site is substantially eliminated. In various embodiments, said medical device comprises a balloon catheter.

BRIEF DESCRIPTION OF THE DRAWINGS

The exemplary embodiments of the present invention will be described in conjunction with the accompanying drawings. The accompanying drawings are included to provide a further understanding of the invention and are incorporated in and constitute a part of this specification, illustrate embodiments of the invention and together with the description serve to explain the principles of the invention. Figures are not drawn to scale.

DETAILED DESCRIPTION OF THE EMBODIMENTS

Embodiments of the present disclosure are directed to retractable sheaths which are constructed of neckable elements that reduce in diameter as the element is elongated, thereby exposing an underlying surface. These embodiments can be utilized with agent delivery constructs, such as a catheter comprising an agent delivery construct for transfer of at least one therapeutic agent to a desired site within a mammalian body. The therapeutic agent delivery construct of the instant invention can comprise additional structures that ensure drug delivery to the target site without significant drug loss during device tracking to the target site. The agent delivery construct comprises an expandable member. In various embodiments, said expandable member is a medical balloon. (As used herein balloon and medical balloon are used interchangeably, unless otherwise noted).

For clarity, the figures, the description and the examples describe and depict an agent delivery construct comprising a medical balloon. However, the invention is not intentioned to be limited to this one embodiment. As described below, expandable members comprising "neckable" sheaths are envisioned as part of this invention. Reference will now be made in detail to embodiments of the present invention, examples of which are illustrated in the accompanying drawings.

Figure 1A:
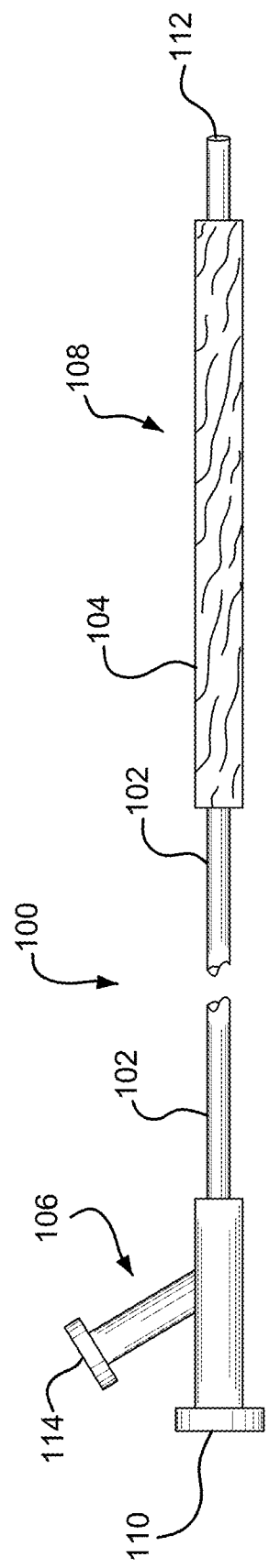
FIG. 1A depicts a side view of a general balloon catheter having an elongated tubular body with a balloon in a first, unexpanded state.

FIG. 1A is illustrative of a balloon catheter 100 having an elongated tubular body 102 with a balloon 104. In one embodiment, balloon 104 may be a length adjustable balloon.

The elongated tubular body 102 has a proximal control end 106 and a distal functional end 108. The balloon catheter also has a proximal guidewire lumen 110 that extends through the length of the elongated tubular body 102 and exits the distal end at a guidewire port 112. The balloon catheter shown is an "Over The Wire" configuration, as commonly known in the art. Alternatively, the catheter could have a guidewire port located midway between proximal and distal ends and therefore have a "Rapid Exchange" configuration, as commonly known in the art. The balloon catheter 100 also incorporates a proximal inflation port 114 that allows fluid communication between the inflation port 114 and the lumen of the balloon 104. The length and inner and outer diameter of the tubular body are selected based upon the desired application of the medical device. The tubular body generally has a circular cross-sectional configuration. However, oval and other cross-sectional configurations can also be used. In one embodiment, said balloon catheter is compatible with 0.038", 0.035", 0.018" or 0.014", 0.010", or similar conventional guidewires.

The tubular body must have sufficient structural integrity to permit the medical device to be advanced to distal vascular locations without bending or buckling upon insertion. Various techniques are known for manufacturing the tubular bodies. In one embodiment, the tubular body is manufactured by extrusion of a biocompatible polymer.

The medical device of the current invention comprises an expandable member with (or without) a structural or substrate layer over the expandable member, at least one therapeutic agent disposed on the expandable member or structural layer, and an outer sheath disposed about the coating. Upon expansion, the outer sheath can be configured to expose the underlying layer. As the underlying layer is exposed, at least a portion of the coating is exposed and delivered to the treatment site. In various embodiments, said expandable member is a medical balloon.

Figure 1B:
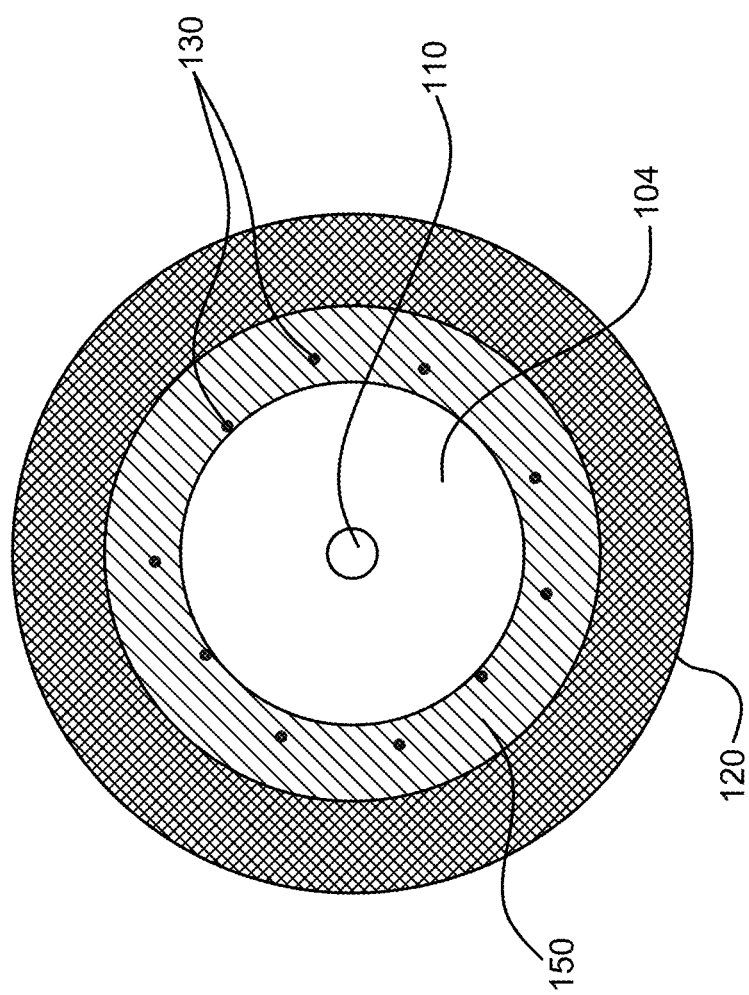
FIG. 1B depict a cross-section of the drug delivery balloon of the invention in its first, unexpanded state.

Upon expansion, with reference to FIG. 1B, the coating 250 is at least partially exposed to the surrounding environment. In various embodiments, upon expansion of the balloon 104 and necking of the sheath 120, the coating 150 is exposed for transference to the surrounding environment. In various embodiments, coating 150 can be tissue adherent and remains adhered to the target tissue even after the device is removed. This embodiment allows for continued drug transfer from the coating at the tissue interface until the tissue coating dissipates from the target tissue, as described in the co-pending and co-assigned U.S. Patent Publication 2010/0233266. In another embodiment, the coating comprises a thixotropic gel.

As used herein, the term "coating" refers to one or more materials disposed on and/or within the surface of a substrate. In the present disclosure, the substrate may include the structural layer, substrate, expandable member, or outer sheath. Said coating may lie completely on the surface or may be incorporated, in whole or in part, within the openings or pores present in a substrate. The latter coating configuration is commonly referred to in the art as "imbibed" or "filled" materials. Coating can comprise a plurality of drug crystals. Coating can comprises a therapeutic agent plus an additional agent to aid in adhesion or tissue uptake.

As used herein, the term "vessel" refers to any luminal or tubular structure within the body to which these constructs can be utilized. This includes, but not limited to, vascular blood vessels, vascular defects such as arteriovenous malformations, aneurysm, or others, vessels of the lymphatic system, esophagus, intestinal anatomy, sinuous cavity, uterus, or other. The embodiments of the present invention are also suitable for the treatment of a malignant disease (i.e. cancer) within or associated with a vessel As used herein, the term "to retract" or "retractable" refers to the act of withdrawing during expansion, thereby causing an underlying layer or surface, e.g., a coating and/or the surface of the expandable member and/or a structural layer, to be exposed to the surrounding environment. As described herein, in various embodiments, "to retract" or "retractable" can refer to the act or ability of necking, tearing, breaking, or otherwise separating to expose an underlying layer or surface. As used herein, the term "to neck" or "neckable" refers to the act of or ability to reduce in transverse dimension, e.g., a width, cross-section or diameter, when being elongated in a longitudinal dimension. With respect to certain embodiments described herein, upon expansion of an expandable member, neckable elements are elongated which cause a reduction in a transverse dimension, e.g., its width, cross-section or diameter, thereby exposing an underlying surface or layer.

Figure 1C:
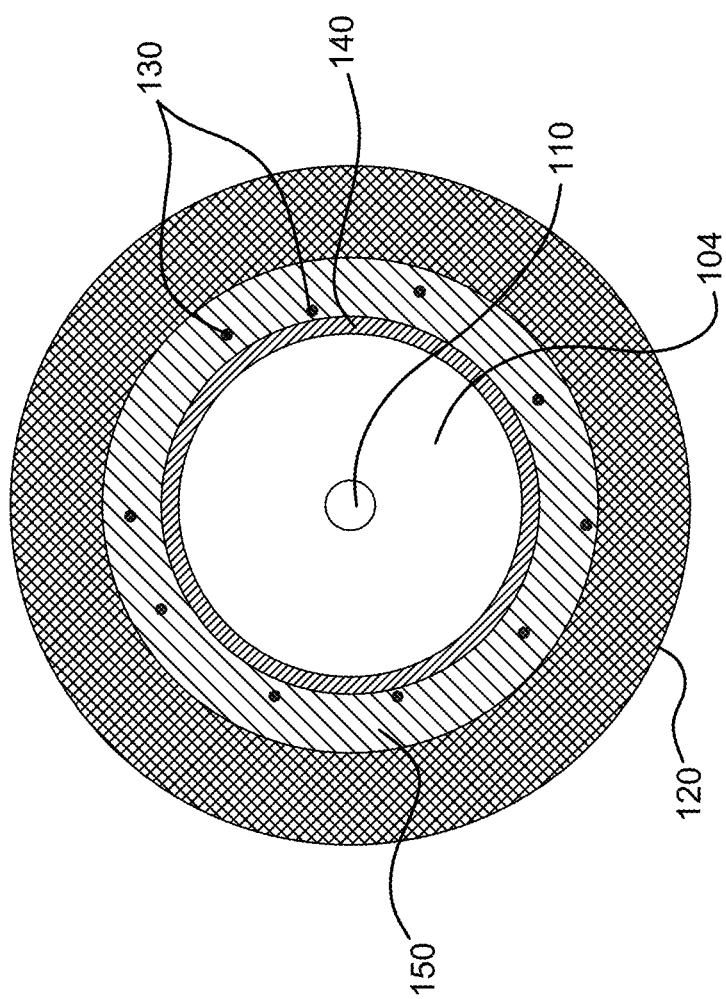
FIG. 1C depict a cross-section of the drug delivery balloon of the invention in its first, unexpanded state having a structural layer.

In various embodiments, as depicted in FIG. 1C, balloon catheter can further comprise a structural layer 140, wherein coating 150 is disposed thereon. FIG. 1C shows a cross-section of an agent delivery construct in its first, unexpanded state. In this embodiment, the construct comprises a balloon 104, a substrate or structural layer or cover 140, a coating 150 on balloon 104 and an outer sheath 120. Coating 150 further comprises at least one therapeutic agent 130. Also depicted is guidewire lumen 110 that extends through the length of the balloon. Structural layer 140 can serve many functions. One of its functions may be to serve as a substrate for uniformly applying the coating 150 to the underlying balloon 104. Since some balloon materials may not be conducive to being uniformly coated, the structural layer can serve as a scaffold to achieve a uniform coating. In addition, if the structural layer comprises an elastomer, the structural layer can help with recompaction of the underlying balloon (see, e.g., U.S. Pat. No. 6,120,477, Campbell, et al., which is hereby incorporated by reference in its entirety for all purposes). In another embodiment, the structural layer can be coated with said hydrophilic coating and said therapeutic agent prior to placement on an expandable member. With such a pre-fabricated, coating construct, any balloon can be converted to an agent delivery construct of the invention. Thus, one embodiment of the invention comprises using a coated structural layer and placing it on any "off the shelf balloon" or OEM balloon to make the balloon a drug delivery balloon.

A structural layer, for example one made according to the examples below, also provides for a uniform tube to be coated at first state which will concentrically/uniformly expand up to a second state. In contrast, conventional Percutaneous Transluminal Angioplasty (PTA) balloons must be coated at second state (in their molded shape) and then be compacted down to a first state. A structural layer can be coated separate from the catheter or balloon on a mandrel, and later assembled onto the balloon with increased manufacturing yields, lower costs, and higher uniformity. As described above, the coating on said structural layer will be covered by an outer sheath.

The structural layer can be made from any material that is compatible with the coating and that can be expanded to accommodate expansion of the balloon. These materials include, but are not limited to ePTFE, fluoropolymers, expanded polyethylene, polyvinylchloride, polyurethane, silicone, polyethylene, polypropylene, polyurethane, polyglycolic acid, polyesters, polyamides, elastomers and their mixtures, blends and copolymers, are all suitable. In one embodiment, said structural layer comprises ePTFE. In another embodiment, said ePTFE is imbibed with an elastomer, such as a thermoplastic copolymer of tetrafluoroethylene and perfluoroalkylvinylether, which can be free of cross-linking monomers and curing agents as described in U.S. Pat. No. 8,048,440, hereby incorporated by reference in its entirety.

In another embodiment of the invention, the surface(s) or outward configuration of the structural layer (or expandable member if a structural layer is not used) may be modified with textures, folds, flaps, invaginations, corrugations, pleats protrusions, spikes, scorers, depressions, grooves, pores, coatings, particles, and the like or combinations thereof. In another embodiment, said depressions, grooves, and/or pores can be used to facilitate protection of the coating during necking of the cover and/or increase the effective surface area over which the coating can be placed. Such surfaces can be etched to increase the effective surface area. In other embodiments, structural layer can comprise a fibrillated microstructure. The fibrils can comprise folds/micropleats to increase the effective surface area. This may help enhance the solvation or hydration cycle. It can also help in reduction of length or profile of the overall medical device.

In another embodiment of the invention and as an alternative to coating a structural layer, which is subsequently combined with an expandable member, the coating material may itself be formed into a structural component that is combined with an expandable member. Such constructs eliminate the requirement for a structural layer per se, yet fully preserve the key functions provided by the coatings of the invention. Such constructs may also improve manufacturability and can be combined with most any expandable member, such as a balloon. For example, where the expandable member comprises a balloon, a tubular form can be cast or otherwise formed from one or more materials of the described coating and disposed over the balloon prior to placement of the outer sheath. In one embodiment, such tubular forms would be made by solvating the coating material(s) into a viscous state and through processes known to the art such as gel extrusion, casting, molding or solution casting/forming formed into the desired tubular shape. The solvent(s) used are subsequently removed to dry or partially dry the tube and makes it easy to dispose over the balloon.

The outer sheath and/or the structural layer can be made from any of the appropriate materials disclosed herein. These structures can be made by extrusion or by layering any of the material described above, e.g. ePTFE. A layer is considered one thickness of a material, which may be wrapped, folded, laid or weaved over, around, beside or under another thickness. A longitudinal pass comprises a distinctive layer or series of layers of material, which are wound to form a region or area distinct from surrounding or adjoining parts. For instance, a pass may comprise multiple layers of a material wrapped at a desired 90° angle relative to the longitudinal axis. This exemplary pass may then be flanked by layers of balloon material wrapped at dissimilar angles in relation to the longitudinal axis, thus defining the boundary of the pass. These layers may be oriented helically or circumferentially (or 90 degrees from the longitudinal axis). In addition, the sheath or structural layer can be helically wrapped at a low or high angle. A low angle wrap of a longitudinally oriented membrane can yield a wrapped construct more distensible than a high angle wrap of a membrane of the same longitudinal orientation, all else being equal (particularly, the strength orientation of the membrane). The angle of the wrap can also vary the amount of stored length/foreshortening, radially or longitudinally. One method for making the structural layer and outer sheath is described below in the examples. In one embodiment, said structural layer can vary in thickness along their longitudinal axes. This will allow for different shapes at the second, inflated diameter. In another embodiment, the construction of the structural layer and/or outer sheath is discontinuous along the longitudinal axis of the components, e.g., one section of the outer sheath is thicker or comprises a different material, or is thinner than another section. In another embodiment, the ends of the structural layer and/or outer sheath are modified to decrease profile of the agent delivery device at the points on the underlying catheter where the structural layer and/or outer sheath are attached. For example, if the structural layer and/or outer sheath are constructed as tubes, a portion of the circumference of their ends may be skived away to open up the tube, i.e., making the ends of the tube only a portion of their original, full circumference. These end "tabs" are then attached to the catheter (using a method detailed below). Because these tabs comprise less material, the profile at the region of their attachment is decreased.

In another embodiment, hygroscopic substances may be incorporated in the coating to accelerate fluid uptake. These materials include, but are not limited to saccharides, dimethyl sulfoxide, decyl methyl sulfoxide, polyvinyl alcohol, glycerol, many salts, including, but not limited to, sodium chloride, zinc chloride, and calcium chloride. Such hygroscopic substances will attract and hold water molecules from the surrounding environment through either absorption or adsorption and help in hydrating the coating to aid in tissue uptake. Such hygroscopic substances may be combined with any of the excipients described herein and/or commonly known in the art.

In another embodiment, the coating can comprise drug-binding agents that act to bind drug particles to one another.

In another embodiment, the coating can comprise a tissue uptake enhancer to increase the dwell time of the therapeutic agent on tissues, tissue uptake of the therapeutic agent, or drug efficacy. Tissue uptake enhancers include integrins, lectins, osmotic agents, membrane disrupters, vasodilators, or polyethylene glycol conjugates. Such uptake enhancers may also include but are not limited to mannitol, decyl methyl sulfoxide, dimethyl sulfoxide, histidine, lysine, lysine acetate, arginine, polyarginine, polyglutamate, poly (glutamate-PEG), sorbitan monostearate, sorbitan tristearate, ascorbyl palmitate, palmitic acid, poly acrylic acid (Carbomer), deoxycholic acid, glucuronic acid. In another embodiment, a therapeutic agent can be complexed with or bonded to a tissue uptake enhancer.

In other embodiments, the coating can comprise a thixotropic agent, mucoadhesive or other agent to enhance the amount of time the coating remains in contact with target tissues, i.e., "dwell time". Such thixotropic agents or mucoadhesive agents may include but are not limited to hetastarch, alginate, poly acrylic acid (Carbomer), polyvinylpyrrolidone (PVP), inclusion complexes of PEG and a cyclodextrin, and biochemically reactive PEG In another embodiment, agents can be incorporated in the coating which serve to bind particles of a therapeutic agent to a target tissue.

In another embodiment, the coating can comprise a stabilizing agent to extend the "shelf life" of a device, such as antioxidants or other known preservatives.

Differential Scanning calorimetry (DSC) can be used to identify and characterize complexes and other physical states of the coating. Fourier Transform Infrared Spectroscopy (FTIR) or Nuclear Magnetic Resonance (NMR) may also be utilized to further characterize complex formation, micelle formation, hydrotrophs, and other formations, which alter the morphology of the therapeutic agent, and to characterize the coating.

A "therapeutic agent" as used herein, which is used interchangeable with the term "drug", is an agent that induces a bioactive response. Such agents include, but are not limited to, cilostazol, everolimus, dicumarol, zotarolimus, carvedilol, anti-thrombotic agents such as heparin, heparin derivatives, urokinase, and dextrophenylalanine proline arginine chloromethylketone; anti-inflammatory agents such as dexamethasone, prednisolone, corticosterone, budesonide, estrogen, sulfasalazine and mesalamine, sirolimus and everolimus (and related analogs), anti-neoplastic/antiproliferative/anti-miotic agents such as major taxane domain-binding drugs, such as paclitaxel and analogues thereof, epothilone, discodermolide, docetaxel, paclitaxel protein-bound particles such as ABRAXANE® (ABRAXANE is a registered trademark of ABRAXIS BIOSCIENCE, LLC), paclitaxel complexed with an appropriate cyclodextrin (or cyclodextrin like molecule), rapamycin and analogues thereof, rapamycin (or rapamycin analogs) complexed with an appropriate cyclodextrin (or cyclodextrin like molecule), 17β-estradiol, 17β-estradiol complexed with an appropriate cyclodextrin, dicumarol, dicumarol complexed with an appropriate cyclodextrin, β-lapachone and analogues thereof, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, AZX100 a cell peptide that mimics HSP20 (Capstone Therapeutics Corp., USA), heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones, sclerosing agents, or a combination thereof. In one embodiment, said therapeutic agent is a hydrophilic agent. In another embodiment, said therapeutic agent is a hydrophobic agent. In another embodiment, said therapeutic agent is paclitaxel.

In various embodiments, the sheath may contain or be marked with radiopaque markers or be constructed to be radiopaque in its entirety. Clinicians to properly track and place an expandable medical device of the invention can use such radiopaque indicators.

Upon or after expansion (i.e., inflation of the medical balloon), the outer sheath causes the coating to be exposed to the surrounding environment. In an embodiment, the outer sheath in accordance with the present disclosure can be configured to retract and expose in a number of configurations and described below.

Figure 2A:
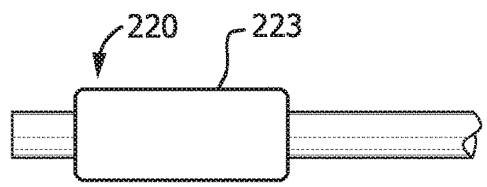
FIGS. 2A and 2F illustrate side views of an embodiment comprising an outer sheath having a neckable element helically wrapped around an expandable member shown in an unexpanded (2A, 2C, and 2E) and expanded state (2B, 2D, and 2F).
Figure 2B:
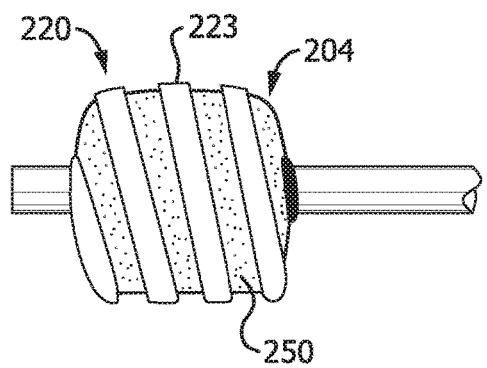
FIGS. 2G and 2J illustrate side views of an embodiment comprising an outer sheath having at least two neckable annular elements adjacent to each other shown in an unexpanded (2G and 2I) and expanded state (2H and 2J).
FIGS. 2K and 2L illustrate side views of an embodiment comprising an outer sheath having at least two neckable elements longitudinally oriented and adjacent to each other in an unexpanded (2K) and expanded state (2L).
Figure 2C:
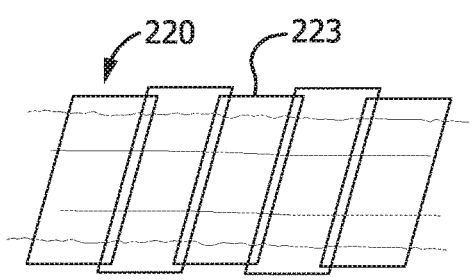
Figure 2D:
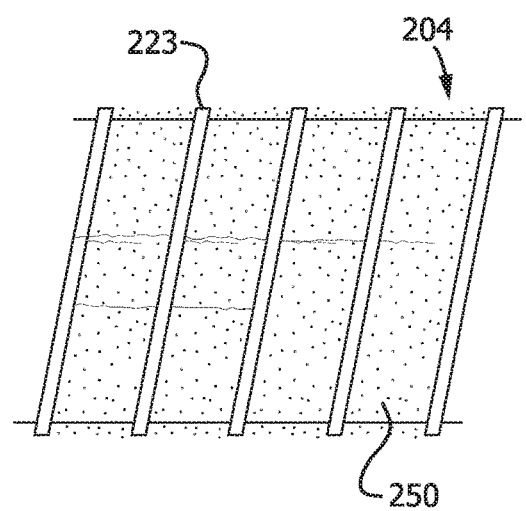
Figure 2K:
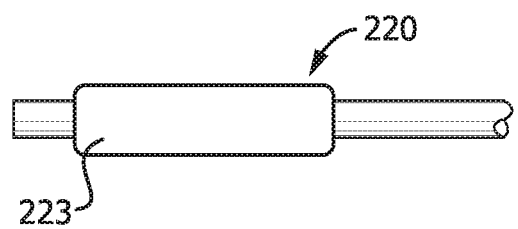
Figure 2L:
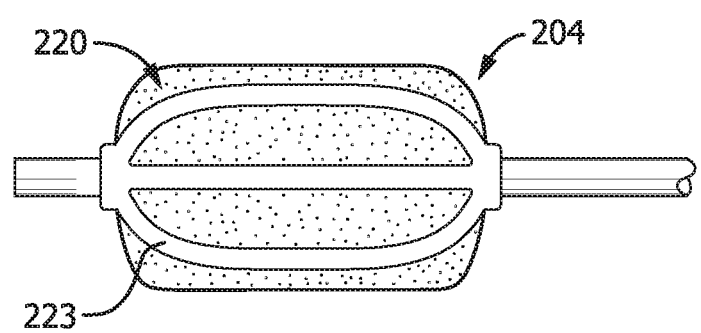

In an embodiment, with reference to FIGS. 2A and 2L, the outer sheath 220 can comprise neckable element 223. Said neckable element 223 is any elongated element configured to reduce in the width dimension as it lengthens. As the underlying expandable member 204 increases in effective surface area or circumference (whether expandable member elastically expands or un-pleats or unfolds), the retractable sheath 220 comprising neckable elements 223 does not correspondingly increase in surface area or circumference, thereby exposing at least a portion of the underlying surface, e.g., a coating 250.

Said neckable element 223 can comprise a strip of film. Said strip can be single-ply or multi-ply. Said film can comprise a plastic and/or an elastic material. Specific neckable materials can include ePTFE membranes, expanded polyethylene, Polyamides, Polyurethanes, Silicones, Polyethylene, or any other sheet or film material possessing the neckable properties. Said film can be an anisotropic material oriented along the expandable member 204 wherein strain can be applied in the weaker direction. On the other hand, balanced materials can also be utilized. Neckable elements 223 can have an initial width of, for example, at least about 1 μm to about 10 mm or more. Neckable element 223 can undergo, for example, at least a 2-, 5, 10-, or 15-fold reduction in width during expansion. Upon expansion of the expandable member 204, the underlying surface, e.g., coating 250, is exposed due to the neckable elements 223 becoming strained and reducing in diameter. In various embodiments, sheath covers about 100% of an underlying surface in a deflated or collapsed conformation and whereby upon expansion, at least about 60% to at least about 90% of the surface of the underlying expandable member can be uncovered or exposed.

In an embodiment, said neckable element 223 can comprise a flattened tubular form. Said tubular form can be formed from a helically wrapped tape and then flattened and disposed about the expandable member, in a longitudinal, circumferential, or helical fashion to form the outer sheath 220. The wrap angle can contribute to the degree of necking. For example, a tubular form can be formed at a high helical wrap angle, and upon expansion, tension is applied to the tubular form, causing the helical angle to change to a lower angle and the diameter of the tubular form to reduce. In an embodiment, coating 250 can also be located within the lumen of the tubular form.

In an embodiment, with reference to FIGS. 2A and 2F, said neckable element 223 or a plurality of neckable elements 223 can be helically wrapped around an expandable member. For example, a helically wrapped, flattened tubular form can be helically wrapped around an expandable member 204. Neckable elements 223 can be constructed to have any suitable width to cover the expandable member 204 with the desired number of helical turns. The smaller the width and the higher the number of helical turns lessens the discontinuity of direct contact between a therapeutic agent and a surrounding tissue upon retraction.

Similarly, in an embodiment, with reference to FIGS. 2G and 2L, at least two neckable elements 223 can be longitudinally oriented and adjacent to each other along the expandable member 204 and attached at a proximal and distal ends of the expandable member 204. In another embodiment, with reference to FIGS. 2G and 2H, said retractable sheath 220 can comprise at least two adjacent annular neckable elements 223. Neckable elements 223 can be constructed to have any suitable width to cover the unexpanded expandable member 204 with the desired number of adjacent elements 223. The smaller the width and/or the higher the number of adjacent elements 223 allows for a more continuous contact of a therapeutic agent to a surrounding tissue.

In an embodiment, the sheath 220 is comprised of a netting or weave of neckable elements 223 where the interstitial spaces open upon stretching. Said neckable elements 223 can be neckable filaments. Said filaments can be sub-micron in width if desired, e.g., 0.1 μm.

Figure 3A:
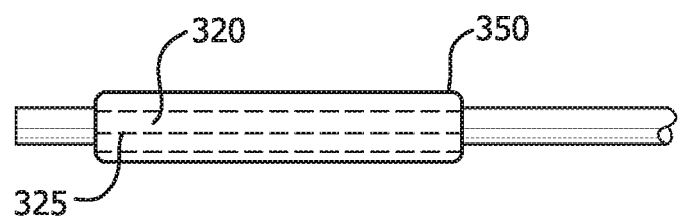
FIGS. 3A to 3B illustrate an embodiment comprising an outer sheath having splittable cover in an unexpanded (3A) and expanded state (3B).
Figure 3B:
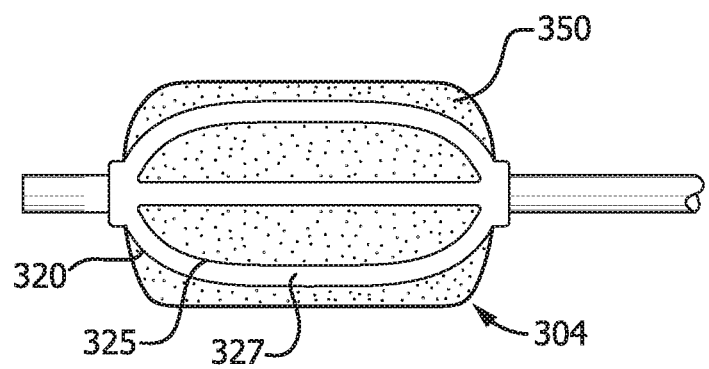

In an embodiment, with reference to FIG. 3A to 3B, the outer sheath 320 can comprise splittable cover. Said splittable cover can comprise a film member 327 or a plurality of film members 327 that have a seam 325 about which the cover will separate and/or split open when the expandable member 304 expands. In one embodiment, seams 325 can be formed at adjacent film members 327. An adhesive can be used to maintain a seam 325 that will not separate or rupture until expansion. In other embodiments, seams 325 can be formed at structurally weakened areas of the film member 327. Structurally weakened areas can comprise a plurality of perforations or thinned regions that rupture upon expansion. Seams 325 can be oriented longitudinally or at a low helical angle. Film member 327 may or may not be neckable. In an embodiment comprising a balloon that is pleated and folded into a collapsed position, the overlying retractable sheath 320 can comprise a plurality of seams 325 that coincide with a plurality of pleats on the underlying balloon in order to facilitate splitting.

In an embodiment, a splittable cover 325 can comprise at least two cover elements 327, each having an edge 325, wherein the edges 325 are adjacent. Upon expansion of an expandable member 304, the edges 325 separate and expose an underlying surface coating 350. The cover elements 327 can be neckable, which further increases the separation distance between two cover elements 327 upon expansion.

Figure 4A:
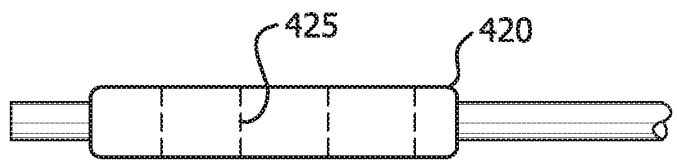
FIGS. 4A and 4B illustrate an embodiment comprising an outer sheath having a neckable cover with structurally weakened seams in an unexpanded (4A) and expanded state (4B).
Figure 4B:
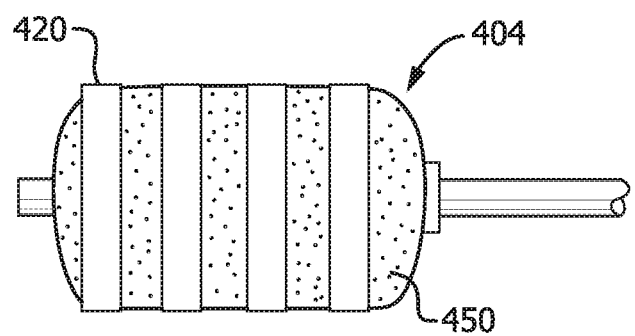

In an embodiment, with reference to FIGS. 4A and 4B, said outer sheath 420 if formed by a neckable sleeve having structurally weak seams 425 in at least one of a circumferential, longitudinal, or helical pattern. Said structurally weak seams 425 will rupture as the expandable member 404 expands, necking the outer sheath 420 fragmented sections and exposing the underlying coating 450.

Figure 5A:
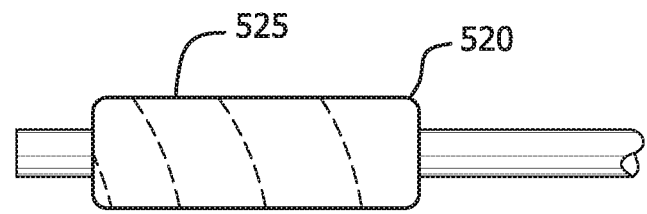
FIGS. 5A to 5B illustrate an embodiment comprising an outer sheath having a splittable casing in an unexpanded (5A) and expanded state (5B).
Figure 5B:
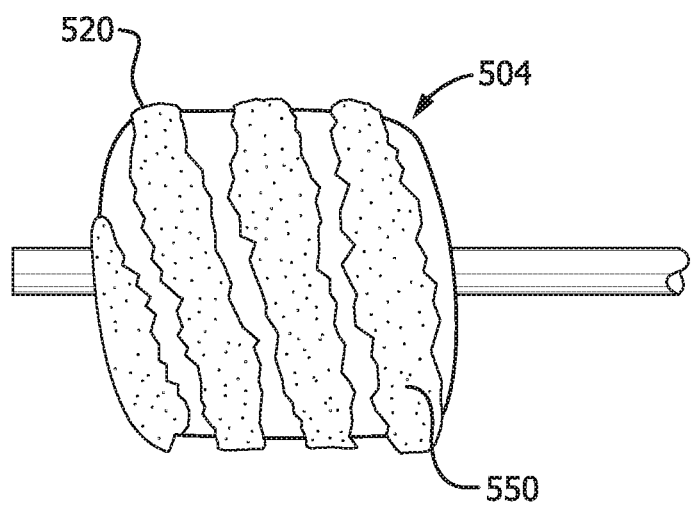
Figure 5C:
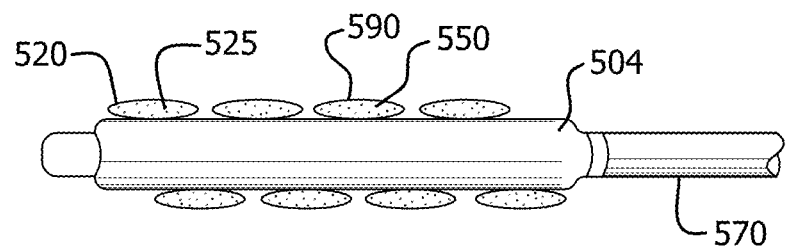
FIGS. 5C to 5D illustrate a lengthwise, cross-sectional view of an embodiment comprising an outer sheath having a splittable casing in an unexpanded (5C) and expanded state (5D).

In an embodiment, with reference to FIG. 5A to 5B, the outer sheath 520 can comprise a splittable casing. Said casing comprises a two-layered construct, having at least an inner face and an outer face and at least partially defining an interior space or lumen. The casing comprises a seam 525 configured to split or rupture along a dimension, e.g., its length, and is positioned on the expandable member 504 so that said seam 525 faces in an outward direction. A coating 550 comprising a therapeutic agent can be located within the lumen 590 of the casing as shown in FIG. 5C. Upon expansion, said casing can spit open and/or rupture along seam 525, exposing the coating 550 to the surrounding environment. As previously described, the seam 525 can be a structurally weakened section. The casing can be oriented longitudinally, helically, or circumferentially relative to the longitudinal axis of the expandable member 504.

Figure 5D:
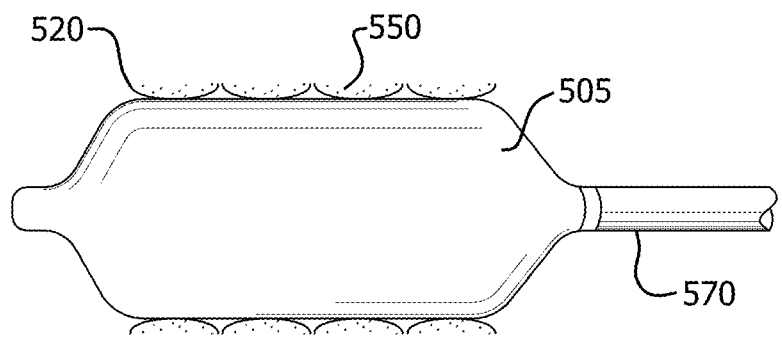

For example, in an embodiment, the casing can be a form having a lumen 590 and a rupturable seam 525 along its length, as shown in FIGS. 5C and 5D, taken at lengthwise cross section FIGS. 5A and 5B, respectively. Also shown in FIGS. 5C and 5D are the expandable member 504 and a catheter 570. Said tubular form can be flattened and disposed about the expandable member 504 to form an outer sheath 520 in a manner where the seam 525 faces outward. Said tubular form can be helically wrapped around the expandable member to form the outer sheath. In other embodiments, said tubular form can be formed into a ring shape and can be circumferentially disposed around balloon. In another embodiment, said tubular form can be longitudinally oriented about the balloon, e.g., attached at a proximal and distal end of a catheter and mounted across the length of the expandable member.

In another embodiment, the coating in combination with a therapeutic agent can be applied to only a portion of an expandable member, e.g., the surface of the balloon or structural, in a discontinuous fashion. Upon retraction, the coating and/or therapeutic agent are delivered to a discrete or more localized site. In contrast, when the coating and/or therapeutic agent is applied in an even distribution to the entire surface of the expandable member, a more uniform delivery of the coating and/or therapeutic agent from the entire circumference of the expandable member can be achieved.

Thus, one embodiment of the invention comprises the drug delivery system comprising an expandable member, such as a balloon, which may comprise a structural layer and/or a substrate, at least one coating containing at least one therapeutic agent, said coating located on the expandable member or structural layer and/or substrate, and an outer sheath.

In another embodiment, said coating comprises a hydrophilic component. In another embodiment, said coating comprises at least one compound selected from the group consisting of benzethonium chloride, poloxamer-188, polyethylene glycol, sodium salicylate, and hydroxypropyl-β-cyclodextrin. In another embodiment, said therapeutic agent is a hydrophilic agent. In another embodiment, said therapeutic agent is a hydrophobic agent. In another embodiment, said therapeutic agent is paclitaxel or a taxane domain-binding drug. In another embodiment, said expandable member further comprises a structural layer. In another embodiment, said structural layer comprises said coating and therapeutic agent.

As used herein, weight percent (wt %) is the dry weight of a coating and/or therapeutic agent after solvent removal. In one embodiment, formulations comprising benzethonium chloride and a hydrophobic agent, such as paclitaxel, the preferred range for said hydrophobic agent are from about 1 wt % to about 70 wt %. In another embodiment, said hydrophobic agent, such as paclitaxel, ranges from about 40 wt % to about 70 wt %. In another embodiment, said hydrophobic agent, such as paclitaxel, ranges from about 20 wt % to about 40 wt %. In another embodiment, said hydrophobic agent, such as paclitaxel, ranges from about 1 wt % to about 20 wt %. In another embodiment, said formulations of benzethonium chloride and a hydrophobic agent, such as paclitaxel, is less than 20 wt % of said hydrophobic agent, such as paclitaxel. In another embodiment, said hydrophobic therapeutic agent is selected from the group consisting of taxane domain-binding drugs, such as paclitaxel, and rapamycin.

In another embodiment, formulations of poloxamer and of a hydrophobic agent, such as paclitaxel, range from about 1 wt % to about 70 wt %, from about 1 wt % to about 50 wt %, from about 1 wt % to about 40 wt %, from about 10 wt % to about 20 wt % of said hydrophobic agent, such as paclitaxel.

In another embodiment, formulations of poloxamer, PEG and of a hydrophobic agent, such as paclitaxel, range from: about 1 wt % to about 70 wt %, about 1 wt % to about 50 wt %, or about 8 wt % to about 40 wt % of a hydrophobic agent, such as paclitaxel; about 1 wt % to about 55 wt %, about 1 wt % to about 40 wt %, or about 5 wt % to about 30 wt % of PEG; and about 1 wt % to about 70 wt %, about 20 wt % to about 70 wt %, about 20 wt % to about 60 wt % of poloxamer, e.g. poloxamer-188. In another embodiment, said hydrophobic therapeutic agent is selected from the group consisting of taxane domain-binding drugs, such as paclitaxel, and rapamycin.

In one embodiment, the agent delivery construct of the invention comprises a coating comprising benzethonium chloride, and a hydrophobic therapeutic agent, wherein said hydrophobic therapeutic is less than 40 wt % of the dry coating. In another embodiment, said hydrophobic therapeutic agent is about 10 wt % to about 20 wt % of the dry coating and benzethonium chloride is about 80 wt % to about 90 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising poloxamer-188, and a hydrophobic therapeutic agent, wherein said hydrophobic therapeutic agent is less than 60 wt % of the dry coating. In another embodiment, said hydrophobic therapeutic agent is about 10 wt % to about 30 wt % of the dry coating and said poloxamer-188 is about 60 wt % to about 75 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising poloxamer-188 and PEG, and a hydrophobic therapeutic agent, wherein said hydrophobic therapeutic agent is less than 50 wt % of the dry coating. In another embodiment, said hydrophobic therapeutic agent is less than 50 wt % of the dry coating and PEG is less than 30 wt % of the dry coating. In another embodiment, said hydrophobic therapeutic agent is about 10 wt % to about 30 wt % of the dry coating and PEG is about 10 wt % to about 20 wt of the dry coating. In another embodiment, said hydrophobic therapeutic agent is about 10 wt % to about 20 wt %, PEG is about 10 wt % to about 20 wt %, and poloxamer-188 is about 50 wt % to about 65 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising benzethonium chloride and PEG, and a hydrophobic therapeutic agent, wherein said PEG is less than 30 wt % of the dry coating and said hydrophobic therapeutic agent is less than 50 wt % of the dry coating. In another embodiment, said PEG is about 10 wt % to about 20 wt % of the dry coating and said hydrophobic therapeutic agent is about 10 wt % to about 25 wt % of the dry coating. In another embodiment, said PEG is about 10 wt % to about 20 wt % of the dry coating, said hydrophobic therapeutic agent is about 10 wt % to about 25 wt % of the dry coating, and benzethonium chloride is about 50 wt % to about 65 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising benzethonium chloride and poloxamer-188, and a hydrophobic therapeutic agent, wherein poloxamer-188 is less than 30 wt % and said hydrophobic therapeutic agent is less than 50 wt % of the dry coating. In another embodiment, poloxamer-188 is about 10 wt % to about 20 wt % of the dry coating and said hydrophobic therapeutic agent is about 10 wt % to about 35 wt % of the dry coating. In another embodiment, said poloxamer-188 is about 10 wt % to about 20 wt %, said hydrophobic therapeutic agent is about 10 wt % to about 25 wt %, and benzethonium chloride is about 50 wt % to about 65 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising hydroxypropyl-β-cyclodextrin, and a hydrophobic therapeutic agent, wherein said hydroxypropyl-β-cyclodextrin is equal to or less than 98 wt % of the dry coating. In another embodiment, said hydroxypropyl-β-cyclodextrin is less than 80 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising sodium salicylate, and a hydrophobic therapeutic agent, wherein said sodium salicylate is about 75 wt % to about 95 wt % of the dry coating. In another embodiment, said sodium salicylate is less than 80 wt % of the dry coating. In another embodiment, said hydrophobic therapeutic agent is selected from the group consisting of taxane domain-binding drugs, such as paclitaxel, and rapamycin.

The therapeutic agents useful in conjunction with the system of the invention may be delivered to the tissue in various structural forms, including but not limited to micelles, liposomes, micro-aggregates, nanospheres, microspheres, nanoparticles, microparticles, crystallites, inclusion complexes, emulsions, gels, foams, creams, suspensions, liquids, and solutions or any combination thereof.

The "expandable member" according to the present invention can be a balloon, expandable catheter, stent, stent-graft, a self-expanding construct, a balloon expandable construct, a combination self-expanding and balloon expandable constructs, a blood vessel graft or a mechanical, radially expanding device which may be expanded, for example via application of a torsional or longitudinal force. Expandable members can also include those which expand due to pneumatic or hydraulic pressure, those which expand due to magnetic forces, those which expand due to the application of energy (for example electrical or ultrasonic (piezoelectric) energy), and those which expand due to osmosis. Expandable members can be placed temporarily in any lumen (e.g. a vessel) by expanding said device and then removed by collapsing said device by a torsional or longitudinal force. In one embodiment, a structural layer and outer sheath is placed on the device such that when it is expanded, the outer sheath retracts and a therapeutic agent will be delivered. In another embodiment, said expandable member allows for blood perfusion to downstream vasculature while implanted in said vessel. This feature may allow for longer implantation durations. In one embodiment, the expandable members may be detached in vivo, and optionally retrieved, from placement devices (e.g., catheters). Examples can be found in U.S. Pat. Nos. 3,996,938, 4,650, 466, 5,222,971, and 6,074,339.

In one embodiment, the expandable member is a medical balloon. Balloons useful in the invention may be blow-molded, may be compliant or semi-compliant or non-compliant and may be of various shapes, for example so called "conformable" or "conforming" or "steerable" balloons. The physical characteristics of said expandable members may also be modified; for example, they may have modulus values that differ from one another. In other embodiments, the expandable members may comprise balloons that are constructed of wrapped films, are fiber-wound, are of variable length, are segmented, and/or have controlled, variable inflation profiles. Such inflation profiles can be, for example, middle-out, where the middle of the balloon increases in diameter first, followed by inflation toward and ultimately including the ends; distal to proximal where the distal end inflates first and inflation progresses proximally; proximal to distal where the proximal end of the balloon inflates first and inflation progresses distally; or ends to middle where both ends of the balloon inflate first and inflation progresses toward the middle of the balloon. Such a construct has the advantage of occluding or limiting flow through the vessel prior to a substantial portion of the therapeutic agent passing through the sheath. (In other words, a "no-flow" or "limited-flow" environment is created once the center portion of the balloon engages with the surrounding tissue.) For example a balloon that inflates first in its longitudinal center region, followed by the ends proximal and distal the center region will cause the coating or coating and therapeutic agent to contact the surrounding tissue first in the center region of the balloon. In other embodiments, a balloon can inflate preferentially in either the distal or the proximal region, with the opposite region subsequently inflating. Other advantages of variable inflation profiles can be realized with use in tapered lumens, for the controlled delivery of endoprostheses, for ballooning of focal lesions with improved accuracy, or for the control of blood flow during the delivery of a therapeutic agent.

Balloons with controlled or variable inflation profiles can be constructed as follows. In one embodiment, a cover may be created by wrapping a film membrane around the balloon. The number of wrapped layers varies along the length of the balloon with fewer layers being positioned over the balloon where expansion is desired to occur first. For example, a middle-out inflation is achieved by wrapping a larger number of layers on the distal and proximal ends of the balloon, leaving fewer layers in the middle of the balloon. The stress exerted by the balloon on the cover layers during balloon inflation meets a lower resistance in the middle of the balloon in this case, allowing the middle to expand first. This same concept can be applied to control inflation in the directions distal to proximal, proximal to distal, or ends to middle simply by varying the layers comprising the cover accordingly such that fewer layers are used where preferential inflation is desired.

In another embodiment, control of the balloon expansion profile can be achieved by preconditioning a portion of the balloon. Preconditioning can occur via repeated blow molding in different sized molds or can occur via one or more partial or full inflations of a portion of the balloon. Preconditioned regions of the balloon preferentially inflate before non-preconditioned regions since preconditioning lessens the force required to initiate an increase in diameter. Constraints (for example, rigid metal rings) can be used as manufacturing aids to inhibit inflation preconditioning in selected regions of the balloon.

Said drug delivery construct can be configured such that control of the balloon expansion profile can be independent of the final (nominal) diameter of the balloon. In one embodiment, the structural layer can be constructed such that although portions of the balloon may inflate in varying sequences, all regions of the balloon will ultimately reach the same final diameter. For example, a drug delivery construct with a middle-out inflation profile can be designed such that the middle portion of the balloon begins to inflate at two atmospheres of pressure. The ends of the same drug delivery construct can be designed to increase in diameter at four atmospheres of pressure. At eight atmospheres, the balloon can be constructed such that the balloon ends reach a diameter essentially equal to the diameter of the middle. At such an inflation pressure, the balloon has essentially an equal diameter along its length. This can be achieved for example, by controlling the expansion profile via the structural layer, but using the underlying balloon to control the final diameter at full inflation.

The agent delivery construct of the invention comprises a structural layer and/or the expandable member that comprises a coating (that may or may not comprise at least one therapeutic agent) on said surface of said structural layer and/or the expandable member. Said coating can render said agent delivery construct very rigid. Due to its rigidity, said agent delivery construct may be difficult to track through tortuous anatomy. Thus, in one embodiment, after applying coating to said structural layer and/or expandable member, the outer sheath is slipped over said structural layer and/or expandable member and then the coating is cracked by pre-stressing, such as through inflating, bending and/or twisting said structural layer and/or the expandable member-outer sheath construct. The coating substrate, e.g., the structural layer, can be engineered to facilitate cracking by providing a rough surface or a surface that helps to concentrate stress in localized areas of the coating such as a cover with small non-distensible regions or areas of higher distention. This allows said agent delivery construct to be more conformable, while not allowing any particulates to escape the outer-sheath prior to treatment. In another embodiment, instead of fully coating the structural layer and/or the expandable member, said coating is applied as "rings" of coating such that in between said "rings" of coatings the structural layer and/or the expandable member is conformable and allow said structural layer and/or expandable member to bend at the uncoated region (allows for flexing). In another embodiment, rather than "rings", the coating and/or therapeutic agent are applied to the structural layer and/or the expandable member as an extruded, helically laid-down, continuous beading. In another embodiment, rather than "rings", the coating and/or therapeutic agent are applied to the structural layer and/or the expandable member as discrete dots or other shapes or discrete patterns. In another embodiment, said rings of coating can comprise the same therapeutic agent and/or different therapeutic agent and/or different coatings.

In another embodiment, the coating and/or therapeutic agent are applied to the structural layer and/or the expandable member in a discontinuous fashion. For example, the amount or thickness of coating may be varied over the surface of the substrate. In instances where drug delivery is desired only at the proximal and distal ends of a stent, for example, coatings applied to only the proximal and distal portions of the structural layer, expandable member and/or outer sheath (leaving the middle portion uncoated) may be desirable, especially for treatment or prevention of stent end stenosis. Coating and/or therapeutic agent compounds may similarly vary in thickness and/or over the area of the structural layer and/or the expandable member.

In another embodiment, the viscosity of the coating and/or therapeutic agent can be modified to improve the dwell time of the agent to the treatment site. In an embodiment, coating can comprise a thickening agent, e.g. a gelling agent.

In another embodiment, said agent delivery construct comprises an underlying medical balloon, a structural layer (optional), a coating comprising a therapeutic agent, and outer sheath wherein said components are mounted on a catheter. In one embodiment, the expanded diameter of said balloon is about 1 mm, about 2 mm, about 4 mm, about 5 mm, about 6 mm, about 7 mm, about 8 mm, about 9 mm, or about 10 mm in diameter with lengths ranging from about 30 to about 150 mm. In another embodiment, said balloon catheter will range in length from about 90 to about 150 cm. In another embodiment, said delivery balloon of the invention is about 5, 6, 7, 8, 9 or 10 French (Fr) in size before introduction into a body vessel, cavity or duct.

In another embodiment, said agent delivery construct comprises an underlying medical balloon, a structural layer (optional), a coating comprising a therapeutic agent, and outer sheath wherein said components are mounted on a catheter but may be detached from the catheter for short or long term implantation.

According to the present invention, said balloon may be formed using any materials known to those of skill in the art. Commonly employed materials include the thermoplastic elastomeric and non-elastomeric polymers and the thermosets.

Examples of suitable materials include but are not limited to, polyolefins, polyesters, polyurethanes, polyamides, polyether block amides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. See, U.S. Pat. No. 5,500,181, for example. As used herein, the term "copolymer" shall be used to refer to any polymer formed from two or more monomers, e.g. 2, 3, 4, 5 and so on and so forth.

Useful polyamides include, but are not limited to, nylon 12, nylon 11, nylon 9, nylon 6/9 and nylon 6/6. The use of such materials is described in U.S. Pat. No. 4,906,244, for example.

Examples of some copolymers of such materials include the polyether-block-amides, available from Elf Atochem North America in Philadelphia, Pa. under the trade name of PEBAX®. Another suitable copolymer is a polyetheresteramide.

Suitable polyester copolymers include, for example, polyethyelene terephthalate and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. In addition, block copolymers wherein the particular block copolymer thermoplastic elastomers in which the block copolymer is made up of hard segments of a polyester or polyamide and soft segments of polyether may also be employed herein.

Specific examples of polyester/polyether block copolymers are poly(butylene terephthalate)-block-poly(tetramethylene oxide) polymers such as ARNITEL® EM 740, available from DSM Engineering Plastics and HYTREL® polymers available from DuPont de Nemours & Co, already mentioned above.

Suitable materials that can be employed in balloon formation are further described in, for example, U.S. Pat. No. 6,406,457; U.S. Pat. No. 6,284,333; U.S. Pat. No. 6,171,278; U.S. Pat. No. 6,146,356; U.S. Pat. No. 5,951,941; U.S. Pat. No. 5,830,182; U.S. Pat. No. 5,556,383; U.S. Pat. No. 5,447,497; U.S. Pat. No. 5,403,340; U.S. Pat. No. 5,348,538; and U.S. Pat. No. 5,330,428.

The above materials are intended for illustrative purposes only, and not as a limitation on the scope of the present invention. Suitable polymeric materials available for use are vast and too numerous to be listed herein and are known to those of ordinary skill in the art.

Balloon formation may be carried out in any conventional manner using known extrusion, blow molding and other molding techniques. Typically, three major steps in the process include extruding a tubular pre-form, molding the balloon and annealing the balloon. Depending on the balloon material employed, the pre-form may be axially stretched before it is blown. Techniques for balloon formation are described in U.S. Pat. No. 4,490,421, RE32,983, RE33,561 and U.S. Pat. No. 5,348,538.

The balloon may be attached to the tubular body by various bonding means known to the skilled artisan. Examples include, but are not limited to, solvent bonding, laser welding, thermal adhesive bonding and heat shrinking or sealing. The selection of the bonding technique is dependent upon the materials from which the expandable element and tubular body are prepared. Refer to U.S. Pat. No. 7,048,713 to Wang for general teachings relating to the bonding of a balloon to a catheter.

The agent delivery constructs provided by the present invention are suitable for a wide range of applications including, for example, a range of medical treatment applications within the body. Exemplary applications include use as a catheter balloon for transferred drug to or placement or "touch-up" of implanted vascular grafts, stents, stent-grafts, a permanent or temporary prosthesis, or other type of medical implant, treating a targeted tissue within the body, and treating any body cavity, space, or hollow organ passage(s) such as blood vessels, the urinary tract, the intestinal tract, nasal cavity, neural sheath, intervertebral regions, bone cavities, esophagus, intrauterine spaces, pancreatic and bile ducts, rectum, and those previously intervened body spaces that have implanted vascular grafts, stents, prosthesis, or other type of medical implants. Additional examples include an agent delivery construct device for the removal of obstructions such as emboli and thrombi from blood vessels, as a dilation device to restore patency to an occluded body passage, as an occlusion device to selectively deliver a means to obstruct or fill a passage or space, and as a centering mechanism for transluminal instruments like catheters. In one embodiment, agent delivery constructs provided by the present invention can be used to treat stent restenosis or treat tissue sites where previously placed drug delivery constructs have failed. In another embodiment, agent delivery constructs as described herein can be used to establish or maintain arteriovenous access sites, e.g., those used during kidney dialysis. In one embodiment, said agent delivery construct comprises a medical balloon used for Percutaneous Transluminal Angioplasty (PTA) in patients with obstructive disease of the peripheral arteries. In another embodiment, agent delivery constructs provided by the present invention can be used to treat coronary stenosis or obstructions.

Other embodiments of the invention comprise a method of delivering a therapeutic agent to a desired location within a vessel comprising, inserting a catheter in a vessel, said catheter comprising an expandable member comprising a coating with a therapeutic agent, a sheath disposed around said expandable member, and wherein said coating is disposed interior to the sheath's outermost layer (or between the surface of the expandable member and the sheath), advancing said catheter to a desired location within said vessel, and expanding the expandable member at the desired location within said vessel, and wherein said sheath necks and exposes a coating. In one embodiment, said expandable member is a medical balloon. In another embodiment, said sheath comprises a fluoropolymer. In another embodiment, the sheath comprises a microstructure comprised of nodes interconnected by fibrils. In another embodiment, said sheath comprises ePTFE. In another embodiment, said therapeutic agent is a hydrophilic agent. In another embodiment, said therapeutic agent is a hydrophobic agent. In another embodiment, said therapeutic agent is paclitaxel. In another embodiment, said coating is hydrophilic. In another embodiment, said expandable member further comprises a structural layer. In another embodiment, said structural layer comprises said coating and therapeutic agent.

Other embodiments of the invention comprise a hydrophilic coating comprising at least one therapeutic agent applied to at least a portion of the exterior surface of an expandable catheter stent, stent-graft, or blood vessel graft over which is placed an outer sheath. Upon expansion of the catheter, stent, stent-graft or graft, the outer sheath disposed over the expandable device necks to expose the coating. In an embodiment, the coating can be located on the proximal and distal sections of the expandable catheter, stent, stent-graft, or blood vessel graft, e.g., to help decrease the incidence of or prevent edge restenosis.

In another embodiment, the expandable medical device of the invention is combined with an occlusion device such as a balloon located proximate the device. Said occlusion device may mitigate the movement of drug far from the treatment site. In one embodiment, the bodily fluids isolated by this system may be withdrawn from the body by aspiration prior to removal of the system.

It is contemplated that a plurality of described embodiments can be attached to a single catheter to facilitate a plurality of drug delivery events or dosages can be delivered with the use of a single device. In the case of a balloon embodiment, a catheter can comprise discrete inflation lumens for each balloon, or some other mechanism for limiting and controlling the inflation to a particular balloon.

Optionally, described embodiments can be configured to apply therapeutic vibrational energy, radiofrequency energy, or the like to enhance drug delivery. Similarly, iontophoresis can be used to aid in the transfer of the therapeutic agent across the outer sheath and into surrounding tissue. In various embodiments, the pressure levels within the expandable member can be pulsed to create multiple, increased pressure events, which can facilitate transfer of the therapeutic agent and/or create multiple drug delivery events.

Another embodiment of the invention comprises a kit comprising a structural layer comprising a coating (further comprising a therapeutic agent) and an outer sheath over said structural layer. Such a kit can convert an off the shelf balloon catheter or catheter into an agent delivery construct of the invention. In another embodiment, said kit comprises an adhesive (including tapes and liquid adhesives) for bonding said structural layer and outer sheath to a balloon catheter.

In another embodiment, said structural layer, outer sheath and adhesive are sterile, placed in a container with an instruction pamphlet explaining how to apply said structural layer and outer sheath onto said balloon catheter. In another embodiment, said balloon catheter is also sterile.

Another embodiment of the invention comprises a PTA or PTCA balloon catheter sheath that extends along a substantial length of the catheter. The sheath at a distal portion comprises a structural layer, drug coating, and an outer sheath about the PTA or PTCA balloon catheter sheath at the location of the PTA or PTCA balloon.

While particular embodiments of the present invention have been illustrated and described herein, the present invention should not be limited to such illustrations and descriptions. It should be apparent that changes and modifications may be incorporated and embodied as part of the present invention within the scope of the following claims. The following examples are further offered to illustrate the present invention.

EXAMPLES

Example 1

Preparation of a Cover

A structural cover was prepared using methods as essentially taught in U.S. Pat. No. 6,120,477 (Campbell, et al.). A film tube was made by helically wrapping 20 layers of a highly fibrillated 5 micron thick ePTFE film (U.S. Pat. No. 5,476,589 to Bacino) at an 83.4° angle to the tubular axis on a 7 mm stainless steel mandrel. Ten layers of the ePTFE were wrapped in one direction and ten layers were wrapped in the opposing direction. The mandrel was baked in an oven set at 380° C. for 6 minutes to fuse the layers together. The resulting tube was removed from the mandrel and "necked" (stretched) down to a diameter below 2.2 mm. This necked tube was placed onto a 2.2 mm stainless steel mandrel and overwrapped with approximately 5 layers of a sacrificial ePTFE film to prevent the tube from wrinkling in the subsequent steps. Next, the tube construct was uniformly compressed to approximately 65% of its original length. The construct was placed in an oven set at the 380° C. for 1 minute and then the sacrificial ePTFE layer was removed. This construct was removed from the mandrel and cut to a 65.0 mm length. In various embodiments, this structural layer may comprise an elastomer to aid in recompaction of the underlying balloon (see, e.g., U.S. Pat. No. 6,120,477, Campbell, et al.).

Example 2

Assembly of a Structural Cover onto a Balloon Catheter

A balloon catheter was purchased from Bavaria Medizin Technologie, Oberpfaffenhofen, Germany (model # BMT-035, article#08PL-604A, with balloon dimensions of 6.0 mm×40 mm). The balloon has the following specifications: a nylon balloon with a 6 atmosphere (atm) nominal inflation pressure and a 14 atm rated burst pressure, a 6 mm nominal diameter, 40 mm balloon working length, mounted on a 0.9 mm guidewire compatible catheter.

The structural tube, as described in Example 1, was centered over the balloon and the ends were wetted with a Loctite 7701 primer (Henkel AG & Co. KgaA, Dusseldorf, Germany). The ends were then fixedly attached to the catheter using five layers of a 6.4 mm width of ePTFE film which were wrapped circumferentially around the balloon ends while Loctite 4981 (Henkel AG & Co. KgaA, Dusseldorf, Germany) was applied to the film.

Example 3

Preparation of an Outer Sheath Comprising a Neckable Element

Figure 6A:
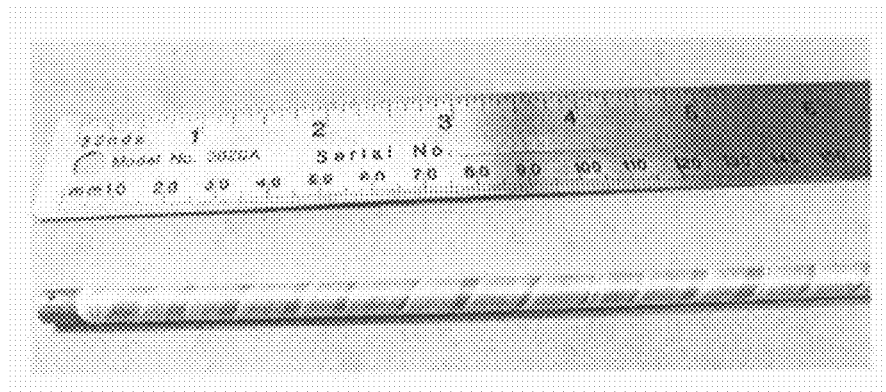
FIGS. 6A through 6C depict the stages of making an agent delivery construct comprising a neckable element helically wrapped around an expandable member.
Figure 6B:
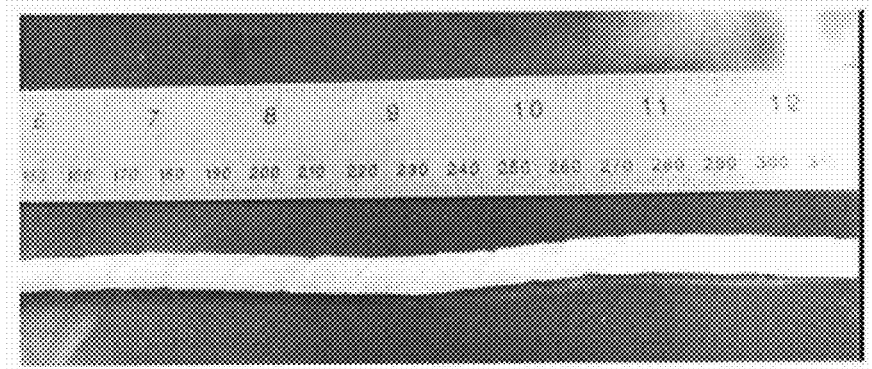
Figure 6C:
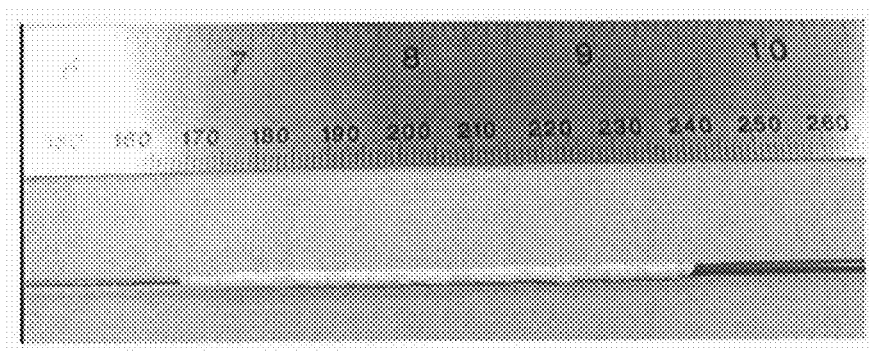

An outer sheath layer was prepared using the following method. As depicted in FIG. 6A, a film tube was created by helically wrapping at least one pass with 50% overlap of a thin ePTFE film tape (as described in U.S. Pat. No. 5,814,405 Branca et al.) at a ~45° angle to the tubular axis on a 6 mm stainless steel mandrel. The resulting tube was removed from the mandrel, as depicted in FIG. 6B. After removal from the mandrel, flattened and helically wrapped around a balloon, structural layer, and a coating to form the outer sheath layer, attached at distal and proximal ends of balloon and excess length was trimmed away. Specifically, the bonded areas were wetted with a Loctite 7701 primer (Henkel AG & Co. KgaA, Dusseldorf, Germany). The ends of the outer sheath layer were then fixedly attached to the balloon using five layers of a 6.4 mm width of ePTFE film. Specifically, the ePTFE film layers were wrapped circumferentially around the balloon ends while Loctite 4981 (Henkel AG & Co. KgaA, Dusseldorf, Germany) was applied to the film. The drug delivery balloon is depicted in FIG. 6C in its unexpanded state.

Example 4

Preparation of an Outer Sheath Comprising a Neckable Element

An alternate outer sheath layer was prepared using the following method. A film tube was created by helically wrapping at least one pass with approximately a 10% overlap of a thin ePTFE film tape slit to a width of approximately 2.54 mm at approximately a 70° angle to the axis on a 2.29 mm mandrel. The ePTFE film had the following properties: thickness was approximately 0.0223 mm; mass per area was approximately 11.74 $g/m^2$; the matrix tensile strength in the strong direction was approximately 35,600 psi; the matrix tensile strength in the direction orthogonal to the strong direction was approximately 4270 psi. The stronger direction is oriented along the length of the film tape. The mandrel comprising the ePTFE layers was baked in an oven set at 380° C. for 2 minutes to fuse the layers together. The resulting film tube was cut into a 60 mm length then centered over the balloon and coating. Both ends were wetted with a Loctite 7701 primer (Henkel AG & Co. KgaA, Dusseldorf, Germany). The ends were then fixedly attached to the catheter using five layers of a 6.4 mm width of ePTFE film which were wrapped circumferentially around the balloon ends while Loctite 4981 (Henkel AG & Co. KgaA, Düsseldorf, Germany) was applied to the film.

Figure 7A:
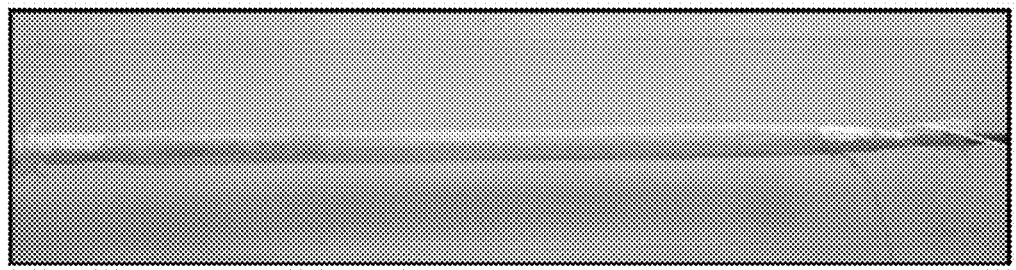
FIG. 7A is an image of the prepared construct in accordance with the present disclosure in a deflated state.
Figure 7B:
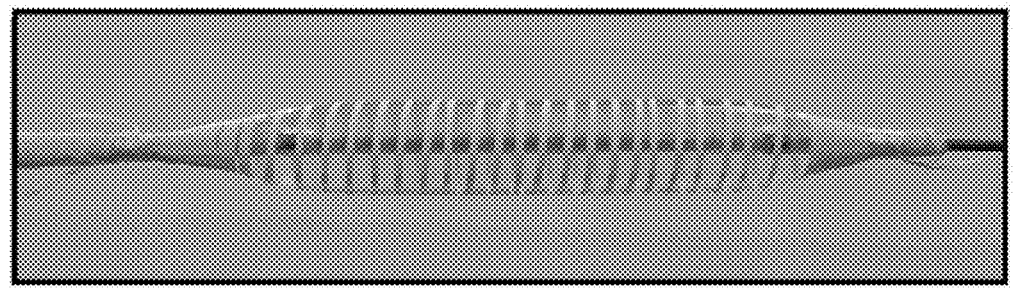
FIG. 7B is an image of the prepared construct of FIG. 7A in an inflated state.

FIG. 7A is an image of the prepared construct in a deflated state, and FIG. 7B is an image of the prepared construct in an inflated state, noting that the underlying balloon surface was exposed upon expansion Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present invention is further directed to embodiments having different combinations of the features described above and claimed below. As such, the invention is also directed to other embodiments having any other possible combination of the dependent features claimed below.

What is claimed is:

1. A medical device comprising:
    an expandable member having an outer surface; and
    a sheath comprising a neckable element having a flattened form along the outer surface of the expandable member, the neckable element being a distinctive layer of material which has a width defined by edges of the distinctive layer of material such that when said distinctive layer of material is helically or circumferentially wrapped around said expandable member in an unexpanded state, the edges of said distinctive layer of material are overlapping or touching one another,
    wherein when said expandable member expands to the expanded state, the expandable member causes the neckable element to lengthen and the width of the distinctive layer to reduce such that the edges of said distinctive layer of material separate from one another, thereby exposing at least a portion of said outer surface.

2. The medical device of claim 1, wherein said neckable element comprises a tubular form having a lumen.

3. The medical device of claim 2, wherein said tubular form is helically wrapped.

4. The medical device of claim 2, further comprising a coating comprising a therapeutic agent disposed within the lumen of said tubular form.

5. The medical device of claim 1, further comprising a coating comprising a therapeutic agent disposed around said expandable member.

6. The medical device of claim 1, wherein said sheath covers 100% of the outer surface in a collapsed conformation and whereby upon expansion, said sheath covers less than 30% of the outer surface.

7. The medical device of claim 1, wherein said sheath covers 100% of the outer surface in a collapsed conformation and whereby upon expansion, said sheath covers less than 20% of the outer surface.

8. A method of delivering a therapeutic agent to a desired location within a vessel or an implanted endoprosthesis, comprising:
    inserting a catheter in a vessel, said catheter comprising:
        an expandable member comprising a coating with a therapeutic agent; and a sheath disposed on said expandable member, wherein said sheath comprises at least one neckable element having a flattened form along the expandable member and comprising a strip of material which has a width defined by edges of the strip material such that when said strip of material is helically or circumferentially wrapped around said expandable member in an unexpanded state, the edges of said strip of material are overlapping or touching one another, wherein said coating is disposed interior to the sheath;

advancing said catheter to a desired location within said vessel; and expanding the expandable member at the desired location within said vessel such that the expandable member causes said at least one neckable element to lengthen and the width of said strip of material to reduce such that the edges of said strip of material separate from one another, thereby exposing at least a portion of said coating.

9. The method of delivering a therapeutic agent of claim 8, wherein said neckable element comprises a tubular form having a lumen.

10. The method of delivering a therapeutic agent of claim 9, wherein said tubular form is helically wrapped.

11. The method of delivering a therapeutic agent of claim 9, further comprising a second coating disposed within the lumen of said tubular form.

12. The method of delivering a therapeutic agent of claim 8, wherein said sheath covers 100% of the coating in a collapsed conformation and whereby upon expansion, said sheath covers less than 30% of the coating.

13. The method of delivering a therapeutic agent of claim 8, wherein said sheath covers 100% of the coating in a collapsed conformation and whereby upon expansion, said sheath covers less than 20% of the coating.

14. The medical device of claim 1, wherein said sheath comprises ePTFE.

15. The medical device of claim 4, wherein said coating comprises at least one compound selected from the group consisting of benzethonium chloride, PEG, poloxamer, sodium salicylate, and hydroxypropyl-β-cyclodextrin.

16. The medical device of claim 4, wherein said therapeutic agent is a hydrophilic agent.

17. The medical device of claim 4, wherein said therapeutic agent is a hydrophobic agent.

18. The medical device of claim 17, wherein hydrophobic agent is selected from the group consisting of taxane domain-binding drugs, such as paclitaxel, and rapamycin.

19. The medical device of claim 1, wherein said expandable member further comprises a structural layer.

20. The medical device of claim 19, wherein a said coating is disposed on said structural layer.

* * * * *